(12) United States Patent
Radl et al.

(10) Patent No.: US 8,309,787 B2
(45) Date of Patent: Nov. 13, 2012

(54) TUNNEL DRESSING FOR USE WITH NEGATIVE PRESSURE WOUND THERAPY SYSTEM

(75) Inventors: Christopher L. Radl, Malvern, PA (US); Kevin P. Klocek, Wynnewood, PA (US); John Karpowicz, Chester Springs, PA (US)

(73) Assignee: Boehringer Technologies, L.P., Phoenixville, PA (US)

( * ) Notice: Subject to any disclaimer, the term of this patent is extended or adjusted under 35 U.S.C. 154(b) by 70 days.

(21) Appl. No.: 12/950,002

(22) Filed: Nov. 19, 2010

(65) Prior Publication Data

US 2011/0284149 A1    Nov. 24, 2011

Related U.S. Application Data

(62) Division of application No. 11/986,941, filed on Nov. 27, 2007, now Pat. No. 8,030,534.

(60) Provisional application No. 60/861,358, filed on Nov. 28, 2006.

(51) Int. Cl.
*A61F 13/00* (2006.01)
*A61M 1/00* (2006.01)

(52) U.S. Cl. .......................... 602/43; 604/313

(58) Field of Classification Search .............. 602/41–59, 602/900, 904; 128/888–889; 604/304–307, 604/315–318; 424/443–449; 156/73.1, 267
See application file for complete search history.

(56) References Cited

U.S. PATENT DOCUMENTS

| | | | |
|---|---|---|---|
| 4,080,970 A | 3/1978 | Miller | |
| 4,787,895 A | 11/1988 | Stokes et al. | |
| 5,358,494 A | 10/1994 | Svedman | |
| 5,447,499 A | 9/1995 | Allaire et al. | |
| 5,478,308 A | 12/1995 | Cartmell et al. | |
| 5,484,399 A | 1/1996 | DiResta et al. | |
| 6,203,563 B1 | 3/2001 | Fernandez | |
| 6,448,462 B2 | 9/2002 | Groitzsch et al. | |
| 6,695,823 B1 | 2/2004 | Lina et al. | |
| 6,855,135 B2 | 2/2005 | Lockwood et al. | |

(Continued)

FOREIGN PATENT DOCUMENTS

WO    9100718    1/1991

OTHER PUBLICATIONS

Argenta, Louis C., M.D. et al., "Vacuum-Assisted Closure: A New Method for Wound Control and Treatment: Clinical Experience," Jun. 1997, Article, Publ. Lippincott-Raven, 563-577.

(Continued)

*Primary Examiner* — Patricia Bianco
*Assistant Examiner* — Ophelia Hawthorne
(74) *Attorney, Agent, or Firm* — Caesar, Rivise, Bernstein, Cohen & Pokotilow, Ltd (57) ABSTRACT

A tunnel dressing for use in treating a tunneling wound using negative pressure wound therapy. The tunnel dressing includes an elongate permeable member having a closed distal end for entering the wound and an open proximal end into which an applicator is removably disposed for guiding the dressing into the wound. The tunnel dressing has a support structure adapted to transport wound exudates away from the wound and to resist compression under suction. The tunnel dressing also has a wound contact surface adapted to minimize tissue entanglement to facilitate removal. The support structure and wound contact surface may be formed from the same material or from two adjacent layers of different material.

4 Claims, 11 Drawing Sheets

U.S. PATENT DOCUMENTS

| | | | |
|---|---|---|---|
| 6,979,324 B2 | 12/2005 | Bybordi et al. | |
| 7,022,890 B2 | 4/2006 | Sessions | |
| 7,381,859 B2 | 6/2008 | Hunt et al. | |
| 7,722,582 B2 | 5/2010 | Lina et al. | |
| 7,754,937 B2 | 7/2010 | Boehringer et al. | |
| 7,758,554 B2 | 7/2010 | Lina et al. | |
| 7,888,547 B2 * | 2/2011 | Masini | 602/58 |
| 7,988,680 B2 * | 8/2011 | Lockwood et al. | 604/313 |
| 2002/0091367 A1 * | 7/2002 | Kusibojoska et al. | 604/378 |
| 2005/0131327 A1 | 6/2005 | Lockwood et al. | |
| 2006/0041247 A1 | 2/2006 | Petrosenko et al. | |
| 2007/0185463 A1 | 8/2007 | Mulligan | |
| 2008/0132819 A1 | 6/2008 | Radl et al. | |

OTHER PUBLICATIONS

Blue Sky Medical, "Negative Pressure Wound Therapy", pamphlet, 2 sheets, website: www/blueskymedical.com.

KCI, V.A.C., "Advanced Dressings", Dedicated Dressings for Specific Wound Applications, brochure, 2005, 6 sheets.

* cited by examiner

TUNNEL DRESSING FOR USE WITH NEGATIVE PRESSURE WOUND THERAPY SYSTEM

REFERENCE TO RELATED APPLICATIONS

This application is a divisional application of U.S. patent application Ser. No. 11/986,941, now U.S. Pat. No. 8,030,534, filed on Nov. 27, 2007, which claims the priority of U.S. Provisional Application No. 60/861,358, filed Nov. 28, 2006.

FIELD OF THE INVENTION

The present invention relates to the treatment of tunneling wounds using suction or negative pressure wound therapy. More particularly, the present invention relates to dressings for use in treating tunneling wounds with suction.

BACKGROUND OF THE INVENTION

When treating wounds, occasionally wounds are encountered that are best described as "tunneling" wounds. A tunneling wound is substantially tunnel-shaped, having an opening at the surface and extending into the flesh, forming a tunnel that is usually longer, and sometimes substantially longer, than the width of the opening. Tunneling wounds can occur by themselves or in combination with a larger open wound, which may include one or more tunneling wounds. Because of their depth, tunneling wounds can present significant risks of infection and can be particularly difficult to heal completely. Thus, it is desirable to provide treatment that removes wound exudates (which can support bacterial growth) and promotes healing of a tunneling wound, including the deepest portions of the wound. Poor healing in the deepest portions of a wound can lead to abscesses if the shallower portion of the wound heals first and closes off the tunnel.

Suction or vacuum can be applied to a tunneling wound to promote wound drainage and wound healing. A challenge in treating tunneling wounds with suction is that it can be difficult to place a dressing into a deep tunneling wound so that the dressing can effectively facilitate the removal of wound exudates. Another challenge in treating tunneling wounds with suction arises because the application of vacuum causes intimate contact between tissue and dressing materials, which can cause the tunnel dressing materials to stick to or become entangled with the wound surface. Entanglement or sticking of the dressing to the wound tissue creates a risk that pieces of the dressing can be broken off and left in the wound when the dressing is removed, and because the tunneling wound is deep, these pieces are not detectable by the clinician removing the dressing. Entanglement or sticking of the dressing to the wound tissue can also cause considerable pain to a patient when the dressing is removed.

Accordingly, it would be desirable to provide a tunnel dressing that can be placed in a tunneling wound so that vacuum can effectively reach the deepest parts of the wound to remove wound exudates and to put beneficial strain on the wound tissue. The dressing should be easy to insert into a tunneling wound. Additionally, the dressing should be easily removable from the tunneling wound without excessive entanglement or sticking to the wound tissue, and strong enough so that it can be removed from the wound in one piece without breaking and leaving small or large pieces in the wound. A tunnel dressing that allows vacuum to effectively reach the deepest parts of the wound also enables fluids to be removed from the deepest parts of the wound, which helps to avoid entrapment of fluid that can lead to an abscess.

Various dressings for use in tunneling wounds during suction therapy have been devised in the prior art. Some dressings employ generally solid rubber (e.g., silicone) or plastic devices having distinct holes or channels formed or cut into them for the purpose of transporting fluids. Other dressings employ a tube-like device having holes extending through the tube walls. There are several disadvantages to these types of devices. Because these devices are constructed from an impermeable material having discrete holes, vacuum cannot be applied uniformly and is thus concentrated on a relatively small portion of the wound surface. Further, the material from which these devices are formed is relatively inflexible, making it difficult and uncomfortable for the patient when the devices are inserted into a wound. Still further, the presence of discrete holes provides space into which large protrusions of tissue can grow, which can cause considerable pain when the devices are removed from a wound.

Still other vacuum dressings employ foam having an open cell structure for transporting fluids. When used for tunneling wounds, such dressings are supplied as a rectangular piece of foam that must be cut by a clinician to match the estimated size of the tunneling wound. A disadvantage of using foam is that foam lacks any significant tensile strength and thus is prone to break when being extracted from the wound, leaving pieces behind within the tunneling wound cavity. Moreover, it is not possible to readily discern when a piece of foam has broken off and remains lodged in the wound, because a torn or cut edge of the foam appears the same as a broken edge. The problem with foam is so significant and well known that after a clinician has cut a piece of foam to size, he or she is trained to tug on the foam piece to try to ascertain if it is strong enough prior to insertion. A further disadvantage of foam is that the foam lacks the stiffness required to push it into many tunneling wounds, so that a clinician often must use a long Q-tip or other ad hoc device to help push the foam dressing into the wound.

Yet other vacuum dressings utilize a tube interconnecting between a suction source at one end and a pad disposed at the opposite end, the tube otherwise having no holes or apertures to communicate vacuum to the wound. In use, the device is placed with the pad deep inside the wound and the tube partly disposed within the wound and extending out from the wound. Any unfilled space surrounding the tube within the wound may be filled with gauze. Numerous disadvantages result from this type of arrangement. Often a tunneling wound is too narrow to allow the pad (with the connected tube) to be placed deep within the wound and to subsequently completely surround the tube with gauze. Further, the device effectively applies vacuum forces only to the wound surface that is in contact with the pad or is in contact with whatever gauze can be packed in around the tube. Thus, the applied suction will generally be able to evacuate exudates from a wound but will be unable to apply suction forces to tissue that is in contact with only the tube. Still further, when the pad is made from foam, all of the problems discussed above with regard to foam dressings may result. In addition, the pad can become detached from the end of the tube and left in the wound when the device is withdrawn. Also, there is no mechanism for introducing the device into a deep tunnel wound other than by pushing on the flexible tube.

SUMMARY OF THE INVENTION

A tunnel dressing is provided for use in treating a tunneling wound with suction, the tunnel dressing comprising an elongate permeable member having a distal end adapted for entering the wound and an opposed proximal end. The permeable member further has an outer surface and a cavity opening onto the outer surface. An applicator can further be provided having a distal portion disposed within the cavity and a proximal portion extending out of the permeable member, the applicator being adapted to guide the dressing into the wound. The cavity can open onto the outer surface at the proximal end of the permeable member, or the cavity can open onto the outer surface at a location between the distal end and the proximal end of the permeable member.

A tunnel dressing is provided for use in treating a tunneling wound with suction comprising an elongate permeable member having a closed distal end adapted for entering the wound, an opposed proximal end, an outer wound contact surface, and an elongate cavity opening onto the proximal end and extending into the permeable member toward the distal end. The cavity is adapted to receive an applicator for guiding the dressing into the wound. The tunnel dressing can further comprise an applicator having a distal portion adapted to be removably received in the cavity and a proximal portion extending outwardly from the permeable member.

A tunnel dressing is provided for use in a treating a tunneling wound with suction comprising an elongate permeable member having a closed distal end adapted for entering the wound, an opposed closed proximal end, an outer wound contact surface, and a cavity opening onto the wound contact surface at a location between the distal end and the proximal end. The cavity is adapted to receive an applicator for guiding the dressing into the wound. The tunnel dressing can further comprise an applicator having a distal portion adapted to be removably received in the cavity and a proximal portion extending outwardly from the permeable member.

A tunnel dressing is provided for use in treating a tunneling wound with suction comprising an elongate member. The elongate member comprises a closed distal end, an opposed proximal end, an elongate cavity opening onto the proximal end, a permeable inner layer surrounding the cavity, the inner layer being adapted for transport of wound exudates, and a permeable outer layer enveloping the inner layer. The outer layer has a wound contact surface. The tunnel dressing can further comprise an elongate applicator removably disposed within the cavity for guiding the dressing into the wound.

A method is provided for treating a tunneling wound with suction. The method comprises providing a tunnel dressing comprising an elongate permeable member having a closed distal end adapted for entering the wound and an opposed proximal end, the permeable member further having an outer surface and a cavity opening onto the outer surface, the tunnel dressing further comprising an applicator having a distal portion disposed within the cavity and a proximal portion extending out of the permeable member, the applicator being adapted to guide the dressing into the wound; inserting the tunnel dressing into the tunneling wound by grasping the proximal portion of the applicator and applying gentle force to push the distal end of the dressing into the wound until increased resistance is detected; placing a wound cover over the tunnel dressing and adhering the wound cover to skin surrounding the wound to form a substantially air-tight seal, the wound cover being adapted to communicate suction via a conduit from a suction source to the wound; and applying suction from the suction source to the wound.

A system for treating a tunneling wound with suction is provided. The system comprises a tunnel dressing comprising an elongate permeable member having a distal end adapted for entering the wound and an opposed proximal end, the permeable member further having an outer surface and a cavity opening onto the outer surface; and an applicator having a distal portion disposed within the cavity and a proximal portion extending out of the permeable member, the applicator being adapted to guide the dressing into the wound; a suction source; a wound cover adapted to form a substantially air-tight seal over the wound dressing by adhering to skin surrounding the wound; and a conduit having an end operatively associated with the wound cover and an opposite end operatively associated with the suction pump, to communicate suction to the wound.

A method of making a tunnel dressing for use in treating a tunneling wound with suction is provided, comprising forming a stack comprising two layers of a first fibrous material sheet sandwiched between two layers of a second fibrous material sheet, the sheets having edges; ultrasonically welding the four layers together to form a unitary piece; trimming excess material away from the unitary piece between the weld and the edges of the sheets to form an article having three sealed edges and an un-sealed edge; and inverting the article to form the tunnel dressing having an internal weld.

A tunnel dressing for treating a wound with suction comprising a generally elongate permeable member is provided. The permeable member comprises a distal end; a proximal end; a cohesive permeable outer wound contact surface; and a permeable internal core. The wound contact surface is adapted to transport wound exudates from the wound tissue to the internal core and is generally free of protrusions that could become embedded in the wound tissue and left behind in the wound tissue when the tunnel dressing is removed. The core has interconnecting interstices extending from the distal end to the proximal end for transporting wound exudates along the elongate member, at least some of the interstices being resistant to complete collapse under the compressive forces of therapeutic suction and in the presence of wound exudates such the core remains capable of transporting fluid. The tunnel dressing has sufficient tensile strength to resist breakage during removal from the wound after exposure to therapeutic suction and wound exudates.

DESCRIPTION OF THE INVENTION

Figure 1:
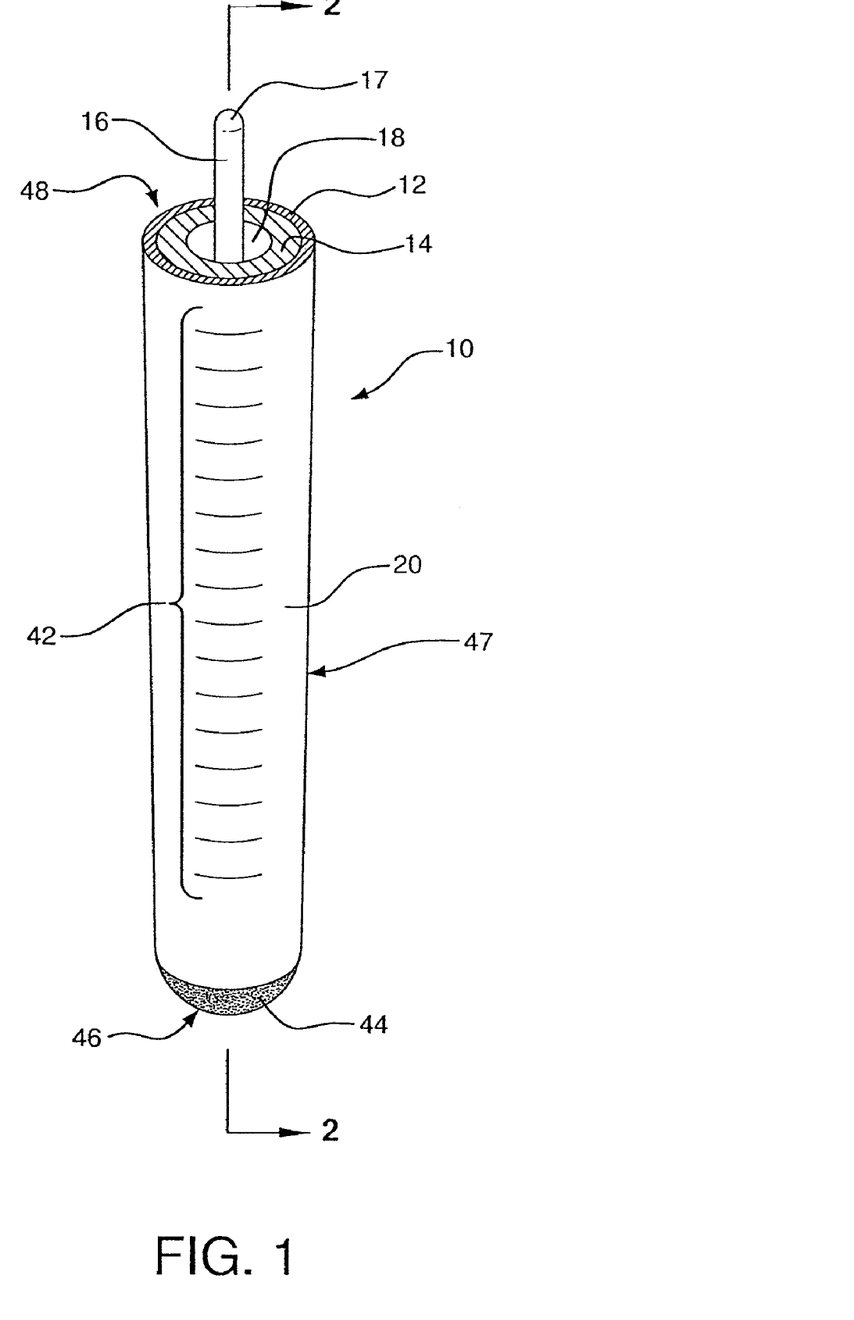
FIG. 1 is a perspective view of a tunnel dressing.
Figure 2:
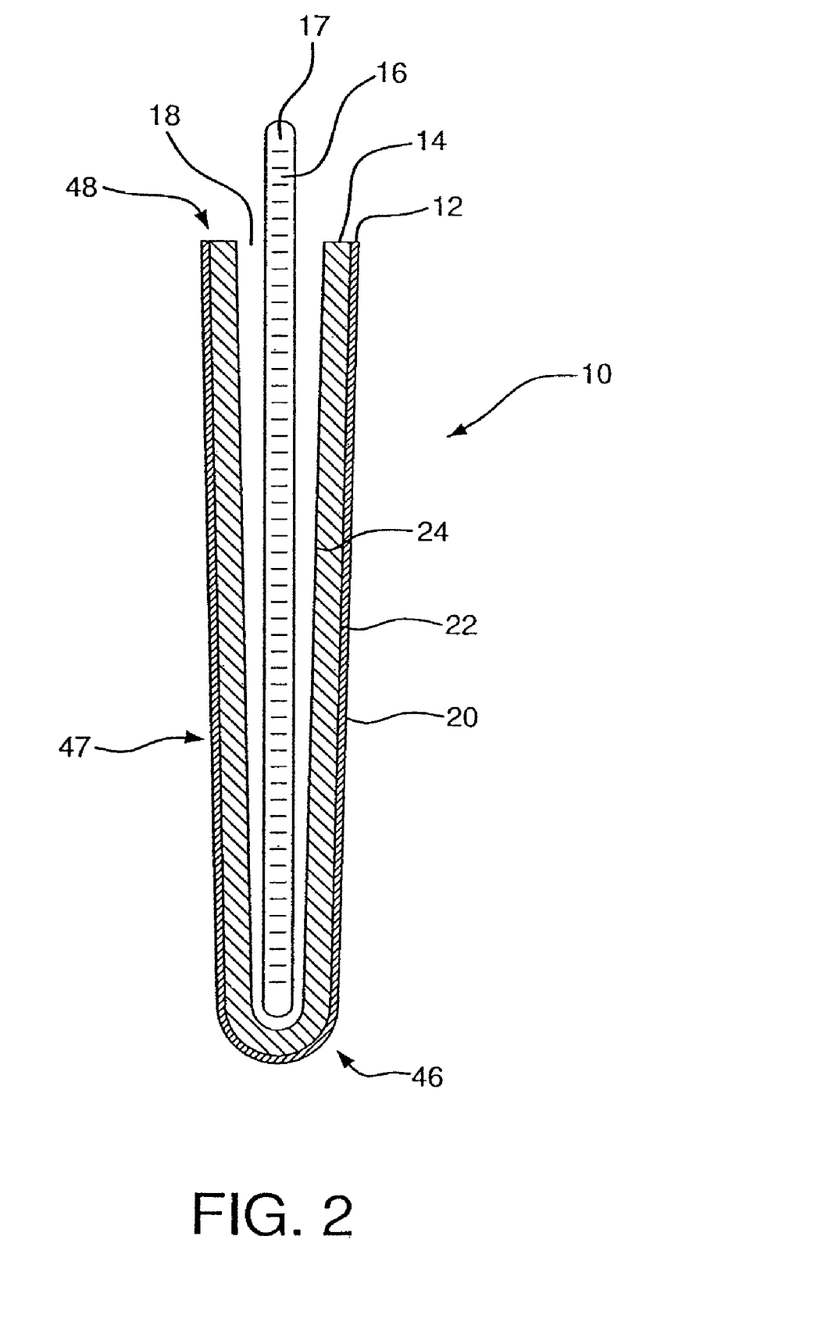
FIG. 2 is a cross-sectional view of an embodiment of the tunnel dressing of FIG. 1 taken through section 2-2.
Figure 3A:
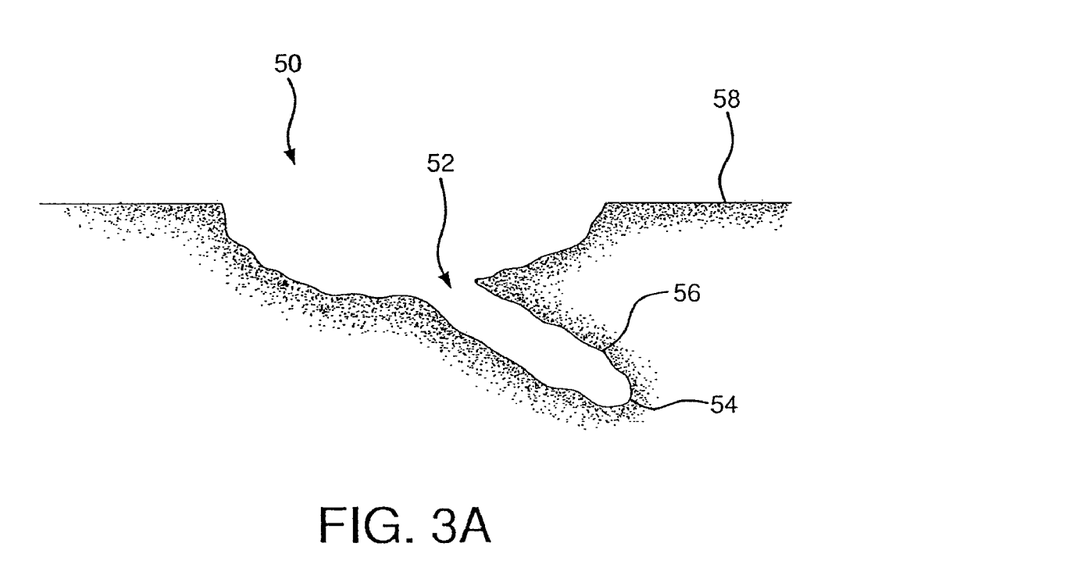
FIG. 3A is a cross-sectional view of an exemplary open wound having a tunneling wound portion into which a tunnel dressing would be inserted.
Figure 3B:
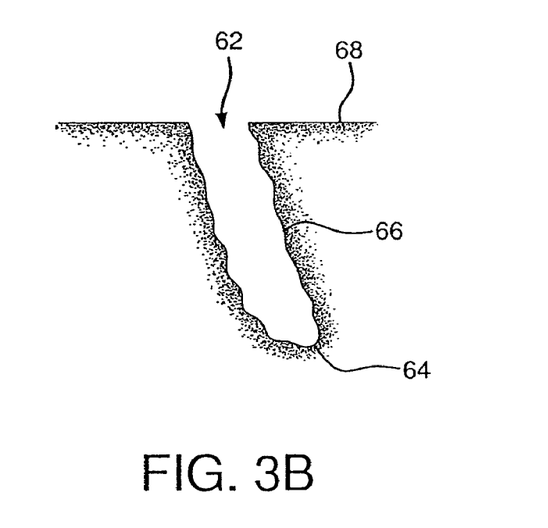
FIG. 3B is a cross-sectional view of an exemplary tunneling wound into which a tunnel dressing would be inserted.

Referring to the drawings, where like numerals identify like elements, there is shown in FIGS. 1 and 2 a tunnel dressing 10 for treating a tunneling wound with suction according to an embodiment of the invention. The tunnel dressing 10 has a generally elongate shape to provide for insertion of the tunnel dressing 10 into a tunneling wound, such as shown in FIGS. 3A and 3B. The tunnel dressing 10 preferably has a closed distal end 46 and an open proximal end 48, and sides 47 spanning between the ends 46, 48, such that the closed end 46 can be inserted into a tunneling wound with the open end 48 protruding outwardly from the wound. The tunnel dressing 10 can have a generally round or circular cross-section, as shown in FIG. 1, or can have a more oblong or ovalized cross-section, depending on the shape of the tunneling wound into which the tunnel dressing 10 will be inserted. The tunnel dressing 10 can be used, as illustrated for example in FIGS. 7A and 7B, for treating a tunneling wound with suction as part of a negative pressure wound therapy system 70.

The tunnel dressing 10 comprises an outer sheath layer 12 contacting an inner core or support layer 14 along at least a portion of an interface 22. The tunnel dressing 10 has a distal end 46 and a proximal end 48. The sheath 12 and the layer 14 can be bonded to each other along their respective edges or across a portion of, or all of, the interface 22. Alternatively, the sheath layer 12 can be slipped over the support layer 14 as a cover and need not be attached thereto. The outer sheath 12 has a wound contact surface 20 and the inner layer 14 has an inner surface 24. The outer sheath 12 is thin relative to the inner layer 14, the inner layer 14 provides structural support to the tunnel dressing 10 and the outer sheath 12 providing a suitable wound contact surface 20. In an embodiment, the support layer 14 is about 0.080 inches thick and the sheath 12 is about 0.003 inches thick.

The outer sheath 12 readily transports fluid therethrough from the wound to the support layer 14 and preferably has sufficient structural integrity so as to not leave fibers behind in the wound. The wound contact surface 20 is cohesive and is sufficiently smooth to allow for easy insertion and removal by minimizing the adherence of new tissue thereto. The inner layer 14 provides structural support to the sheath 12 and comprises a permeable fibrous structure to allow for transport of exudates lengthwise along the dressing 10 (i.e., in the direction from the distal end 46 to the proximal end 48) and out of the wound when suction is applied by a negative pressure wound therapy system 70. Because the inner layer 14 may include fibers that are only loosely coupled together, the outer sheath 12 serves to retain loose fibers so they are not left in the wound when the dressing 10 is removed.

The sheath 12 is made from a permeable material adapted to allow wound exudates to be transported therethrough, such that when the wound is subjected to suction, wound exudates can be drawn away from the wound surface. Under suction, exudates are drawn through the sheath 12 and into the layer 14, and then through the layer 14 towards the proximal end 48 of the tunnel dressing 10. The sheath 12 is preferably made from a fibrous material having a high structural integrity, such as nonwoven polyester, with tightly coupled fibers that are not prone to shed into the wound. The wound contact surface 20 of the sheath 12 has a relatively smooth structure as can be achieved by calendaring the material of the sheath 12. The fibers of the sheath 12 are preferably long continuous fibers that can be bonded together with heat.

The contact surface 20 is substantially without very large voids or discontinuities (i.e., voids greater than an order of magnitude larger than the average interstitial space between adjacent fibers), in order to minimize the tendency for large protrusions of wound tissue to become entangled in the tunnel dressing 10. Rather, the contact surface 20 comprises a large number of small openings or interstitial spaces between fibers which enables good fluid transport. The small interstitial spaces between fibers in the contact surface 20 also minimize tissue entanglement and prevent any loose fibers from the layer 14 from becoming embedded in the wound tissue and left behind in the wound. Further, the fibers of the sheath 12 generally do not protrude or terminate beyond the wound contact surface 20, thus minimize the possibility that fibers can be embedded in wound tissue or left behind in wound tissue when the dressing 10 is removed after the application of suction therapy.

The permeable nature of such a fibrous material of the sheath 12 allows for application of vacuum to more of the wound surface than can be obtained with dressings having discrete holes or channels. The polyester fibers generally do not absorb fluids, meaning that they do not swell when subjected to moisture but instead allow liquid to be conducted along their surface and through the fibrous material under the force of applied suction. One such material is sold by Ahlstrom Corp. as Hollytex 3257, a spunbond polyester sheet having a highly calendared surface. Other such materials having slightly larger interstitial spaces are Hollytex 3256 and Hollytex 3249. Other similar or equivalent materials can be used. The sheath 12 is preferably made from a sheet of material, the sheet being formed by heat sealing or welding into a sheath-like shape with a closed end onto the support layer 14, as shown in FIGS. 1 and 2. The heat sealing or welding process provides additional strength to the sheath 12, and thus to the dressing 10, which eliminates or substantially reduces the risk that a portion of the tunnel dressing 10 can break off and be left in a tunneling wound.

The core or support layer 14 is made from a permeable material having a structure that imparts compression resistance to enable the layer 14, and thus the tunnel dressing 10, to resist collapse or compression under the force of therapeutic suction, such as that applied during negative pressure wound therapy. A negative pressure wound therapy system can apply negative pressures to a wound in the range of about 5 mm Hg to about 500 mm Hg, preferably in the range of about 25 mm Hg to about 200 mm Hg, and most preferably in the range of about 30 mm Hg to about 75 mm Hg.

The layer 14 is also adapted to transport wound exudates that are drawn from the wound through the sheath 12 into the layer 14, so that the exudates can be removed from the dressing 10 by suction applied at the end 48 of the dressing 10 by a negative pressure wound therapy system 70. The layer 14 is preferably made from a fibrous material such as nonwoven polyester felt. During the felting process, fibers become oriented in multiple directions, which improves the compression resistance of the layer 14. The fibrous material of the layer 14 preferably has interconnected interstices throughout, at least some of the interstices resisting complete collapse under the compressive forces resulting from negative pressure wound therapy and in the presence of wound exudates so that the interstices remain capable of transporting fluid through the dressing. As with the fibers used to form the sheath 12, the polyester fibers of the support layer 14 generally do not absorb fluids, meaning that they do not swell when subjected to moisture but instead allow liquid to be conducted along their surface and through the fibrous material under the force of applied suction. One such material is felt made from polyester fibers, the material having a thickness of about 0.080 inches and a basis weight of 5 ounces per square yard.

In an embodiment, the tunnel dressing 10 is about 6 inches long and about 0.25 inches in diameter (i.e., a length to diameter ratio of about 24), although the dressing 10 can be made in a wide range of lengths, diameters, and length/diameter combinations. The fluid transport properties of the support layer 14 enable the withdrawal of exudates by suction from very deep wounds. The layer 14 is preferably made from a sheet of material, the sheet being formed by heat sealing into a sheath-like shape with a closed end as shown in FIGS. 1 and 2 such that the inner surface 24 of the layer 14 faces itself and forms a cavity 18 within the dressing 10.

Figure 10:
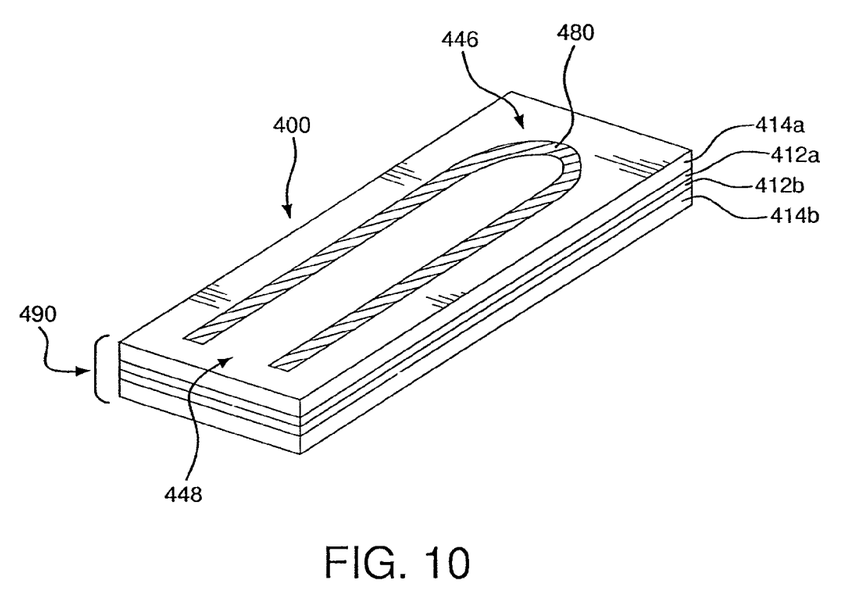
FIG. 10 is a perspective view illustrating a method of making a tunnel dressing.

The dressing 10 comprising the support layer 14 and the sheath 12 can be made from layered sheets of material, as depicted in FIG. 10. Two sheets 412a and 412b of material for forming the sheath 12 (e.g., spunbond polyester) are sandwiched between two sheets 414a and 414b of material for forming the support layer 14 (e.g., polyester felt) to form a stack 490 of layered materials. Next, the four layers are preferably ultrasonically welded together along a generally U-shaped weld 480 forming essentially three sides of a rectangle, leaving a non-welded portion forming essentially a fourth side of the rectangle. The corners of the rectangle can be more rounded or less rounded depending on the desired configuration of the dressing 10.

It is contemplated that the four layers could be formed by layering a sheet of material 412 on top of a sheet of material 414 and folding the two layers over on themselves along a fold line, so that the stack only need be welded along a generally L-shaped weld line forming two sides of a rectangle, the third closed side being formed by the fold line. It is further contemplated that the stack could be welded along a generally box-shaped weld line forming essentially all four sides of a rectangle. Then, the weld along a portion forming essentially one side of the rectangle can be cut off to create a non-welded opening. Alternatively, all four welds can be left in place and an opening can be cut through one of the layers 414a and one of the layers 412a to enable access to a cavity formed between the layers 412a and 412b.

Next, the layers of material 414a, 412a, 412b, and 414b are cut around the weld 480 to remove the excess material between the weld 480 and the edges of the stack 490, as well as any excess material between the end of a U-shaped or L-shaped weld 480 and the edges of the stack 490 at the non-welded opening. The remaining article has two layers of support material 414a and 414b on the outside surrounding two layers of sheath material 412a and 412b, a weld 480 on essentially two or three edges of the article that is relatively hard and jagged compared with the layers of material, and an opening at one end of the article where the layers are not welded together. Finally, the article is inverted or turned inside out to form a tunnel dressing 10 having an internal weld 480, an outer sheath 12 of spunbonded material, an inner core or support layer 14 of felt, and a cavity 18 disposed within the inner support layer 14 (i.e., between the sheets 414a and 414b). Cavities also exist between each of the sheets 414a/414b and its corresponding adjacent sheet 412a/412b.

The resultant tunnel dressing 10 has a closed distal end 446 and an open proximal end 448, with the weld 480 extending internally along the length of the dressing from the closed end 446 to the open end 448. The weld 480 imparts additional tensile strength to the dressing so that after the application of suction to a wound having the dressing 10 therein, the dressing 10 can be removed without breaking and without leaving any remnants of the dressing 10 in the wound cavity. The weld 480 also extends internally along the distal closed end 446 of the dressing 10, imparting additional strength to the closed end 446 to inhibit, or to assist in preventing, the applicator rod 16 from pushing through the closed end 446 when the dressing 10 is being inserted into a wound.

The tunnel dressing 10 is preferably inserted into a tunneling wound using a semi-flexible applicator rod 16 removably disposed within the cavity 18. Exemplary wounds are illustrated in FIGS. 3A and 3B. The applicator rod 16 is preferably made from a relatively thin piece of material that is sufficiently rigid to transmit force along its length as required to gently push and guide the dressing 10 into the wound, yet is sufficiently flexible to follow the contours of the tunneling wound as the dressing 10 is being inserted. The rod 16 is preferably less flexible than the dressing 10. The rod 16 can comprise plastic, wood, metal, paper, and/or other suitable material.

Figure 7A:
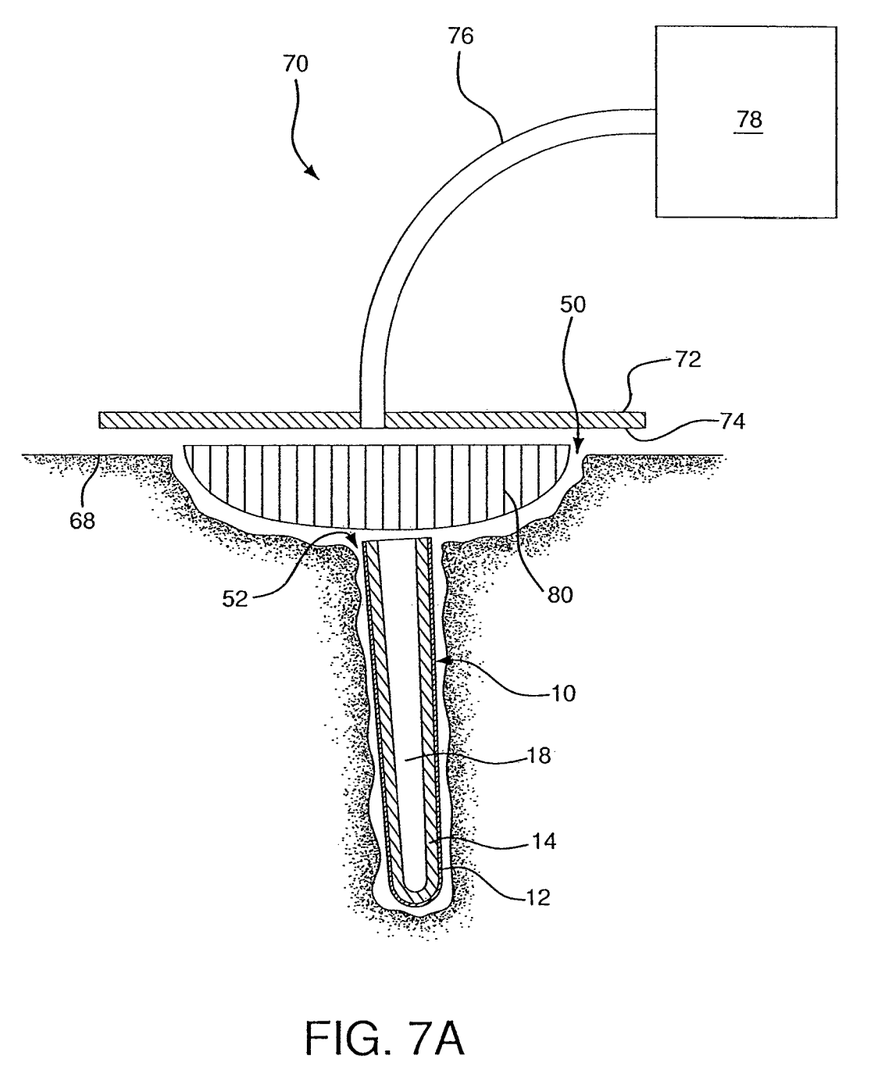
FIG. 7A is a cross-sectional view showing a tunnel dressing as in FIG. 1 inserted into a tunneling wound as in FIG. 3A, wherein suction is applied to the wound.
Figure 7B:
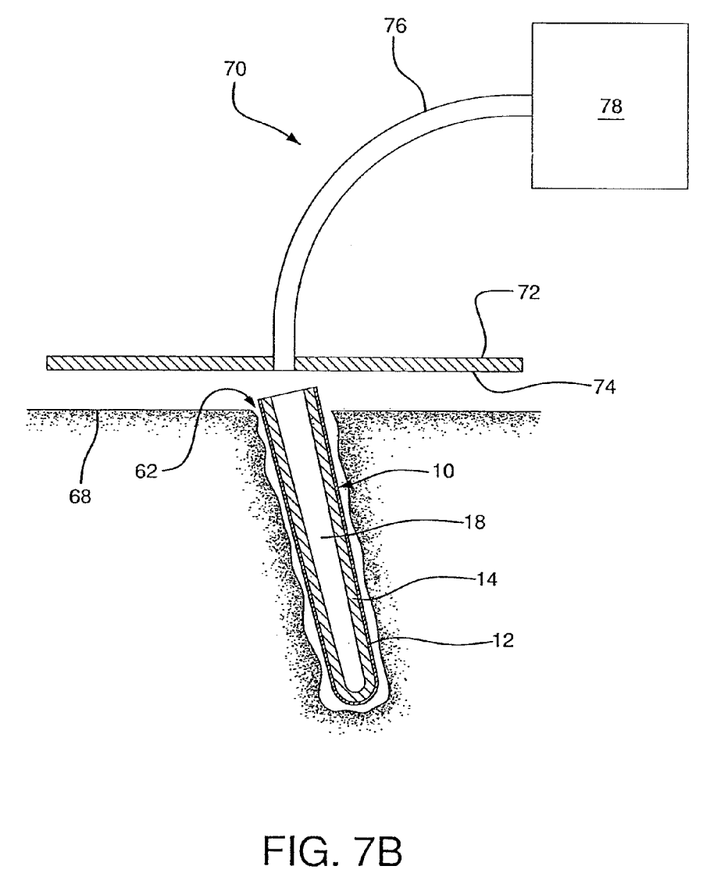
FIG. 7B is a cross-sectional view showing a tunnel dressing as in FIG. 1 inserted into a tunneling wound as in FIG. 3B, wherein suction is applied to the wound.

The rod 16 engages the far end of the tunnel dressing 10 so that when a clinician pushes on the rod 16, force is transmitted to the distal end 46 of the tunnel dressing 10, the end 46 thereby pulling the remainder of the tunnel dressing 10 into the tunneling wound. In a tunneling wound 62 such as shown in FIGS. 3B and 7B, the tunnel dressing 10 can be used alone to dress the wound cavity for treatment of the wound 62 with suction. In an open wound 50 including a tunneling portion 52 such as shown in FIGS. 3A and 7A, the tunnel dressing 10 can be used in combination with a wound packing 80 such that the tunnel dressing 10 dresses the tunneling portion 52 and the wound packing 80 dresses the remainder of the wound cavity 50 for treatment of the wound 50 with suction. Many wound packings 80 are known in the art, including packings disclosed in U.S. patent application Ser. No. 10/981,119, filed on Nov. 4, 2004 and commonly assigned with the present application.

Providing the tunnel dressing 10 in a sheath-like shape having a closed distal end 46 is advantageous compared with attempting to push a flat sheet into a tunneling wound using a rod. In particular, the dressing 10 can easily be guided into a deep tunneling wound with only a small amount of force, the smooth material of the contact surface 20 on the tip 46, in conjunction with the contact surface 20 on the sides 47, guiding the dressing 10 as the rod 16 is gently pushed inwardly into the wound. Thus, pain is minimized and the dressing 10 can be placed as far as desired into the wound.

Figure 4:
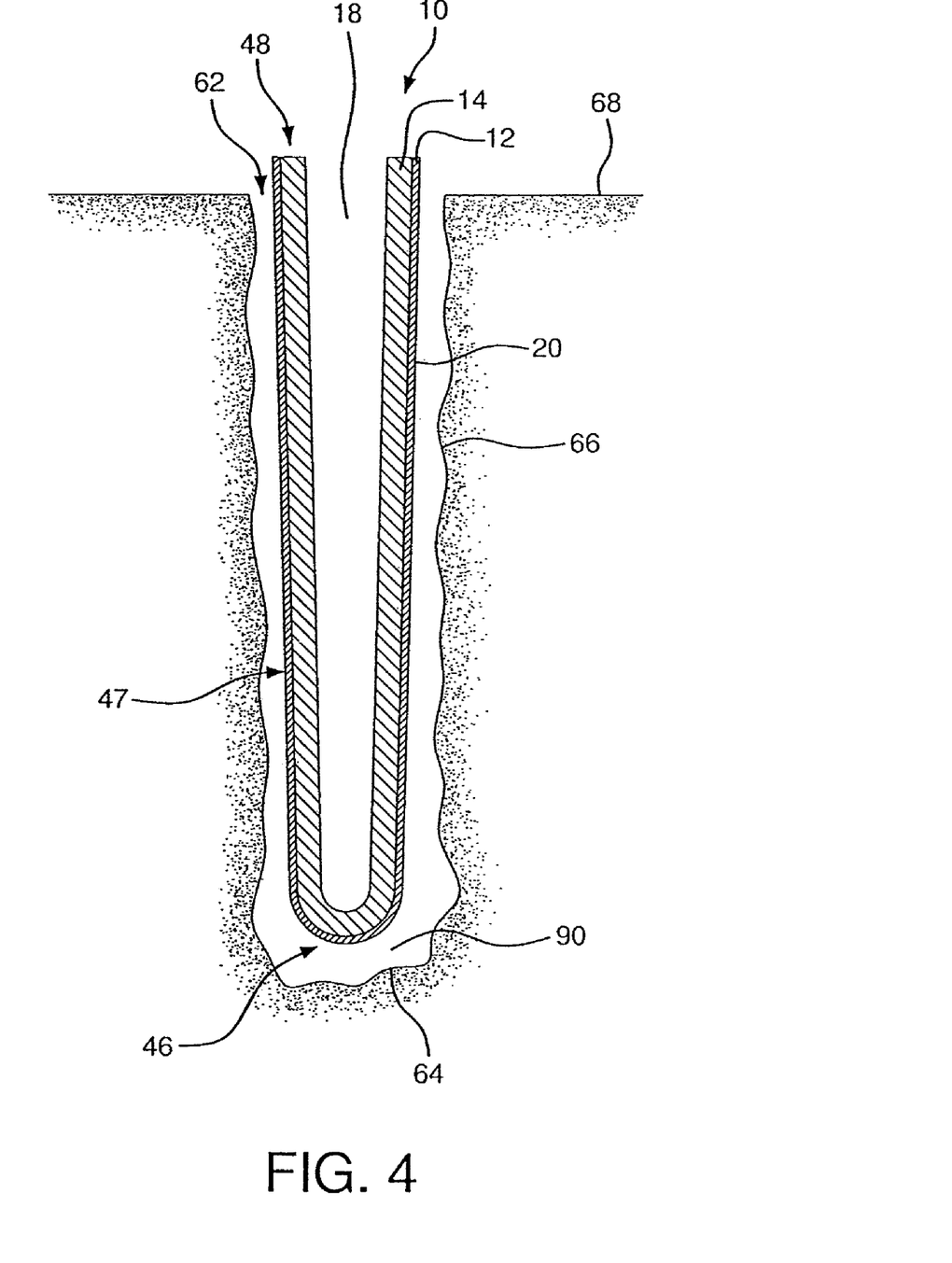
FIG. 4 is a cross-sectional view showing a tunnel dressing as in FIG. 1 inserted into a tunneling wound as in FIG. 3B.

For clarity of description, the process of inserting the tunnel dressing 10 is generally described herein with reference to a tunneling wound 60 as illustrated in FIGS. 3B, 4, and 7B, it being understood that the description applies similarly to an open wound 50 having a tunneling portion 52 as illustrated in FIGS. 3A and 7A. A tunneling wound 62 in a tissue surface 68 can be defined by walls 66 and a bottom end 64. Alternatively, a tunneling wound can be defined as a wound 50 in a tissue surface 58 having a tunneling portion 52 defined by walls 56 and a bottom end 54.

To insert the tunnel dressing 10 into a tunneling wound 62, a clinician grasps the rod 16 at a proximal end 17 protruding from the open end 48 of the dressing 10. A dressing 10 should be selected that is somewhat longer than the anticipated depth of the wound 62 so that a portion of the dressing 10 remains protruding from the wound 62 after insertion. The protruding portion of the dressing 10 can be readily grasped for removal. The clinician gently guides the tunnel dressing 10 into the tunneling wound 62 by applying light force along the length of the rod 16. The rod 16, the sheath 12, and the layer 14 are sufficiently flexible to follow the countours of the walls 66 of the tunneling wound 62 as the dressing 10 is inserted thereinto. When the clinician feels increased resistance indicating that the dressing 10 is reaching the end 64 of the wound 62, the clinician can gently withdraw the rod 16, leaving the dressing 10 in place within the wound 62.

Withdrawal of the rod 16 leaves a small elongate cavity 18 within the dressing 10 extending from the open end 48 to near the closed end 46. The cavity 18 serves a functional purpose during use of the dressing 10, in addition to providing a receptacle for the applicator rod 16 during insertion of the dressing 10. The cavity 18 has less resistance to collapse than the permeable material of the support layer 14 or of the sheath 12, and therefore enables the tunnel dressing 10 to be compacted somewhat in width as the wound cavity 62 is drawn together under applied suction without hampering the fluid transport capacity of the layer 14 or the sheath 12 of the dressing 10.

In order to encourage tissue growth in the end 64 of the wound 62 when suction is applied to the dressing 10, the clinician preferably partially withdraws the dressing 10 slightly away from the wound end 64 before suction is applied by grasping a portion of the dressing protruding from the wound 62 and pulling gently outwardly. The preferred position of the tunnel dressing 10 within the wound 62 is shown schematically in FIG. 4, the dressing 10 being fully inserted into the wound 62 and then partially withdrawn slightly to leave a space 90 for tissue growth in the wound end 64. The space 90 is preferably about 1 centimeter from the wound end 64 to the dressing 10, recognizing that a larger or smaller space may be desired depending on the depth, width, exudate rate, and other characteristics of the wound 62. Once the dressing 10 is in place, if a larger portion of the dressing 10 is protruding from the wound 62 than desired or than needed for later removal of the dressing 10, the excess dressing 10 may be cut off to preferably leave a small protruding portion.

After the tunnel dressing 10 has been installed into the wound 62, a conventional vacuum or negative pressure wound therapy system can be used to apply suction to the wound. Such a negative pressure wound therapy system 70 is shown generally in FIGS. 7A and 7B, the system comprising a suction source 78, a wound cover 72 having an adhesive coating 74 on one side for adhering to skin surrounding a wound, and a conduit 76. The conduit 76 has an end operatively associated with the wound cover 72 and an opposite end operatively associated with the suction source 78 for communicating suction from the suction source 78 to the wound 62 beneath the wound cover 72. Non-exhaustive examples of applicable vacuum or negative pressure wound therapy systems are described in detail, for example, in U.S. patent application Ser. No. 11/786,475, filed on Apr. 12, 2007 and in U.S. patent application Ser. No. 11/181,128, filed on Jul. 14, 2005, both commonly assigned with the present application. The suction source 78 can comprise a stationary suction system such as those commonly found in hospitals, or a portable pump or bellows or other equivalent mechanism for providing and delivering a therapeutic level of suction to the wound.

For a tunneling wound 62 of the type shown in FIG. 3B, a wound cover 72 can be placed directly over the tunnel dressing 10, as shown in FIG. 7B. The cover 72 comprises a semi-permeable material that is generally air-tight but allows vapor and/or moisture to be transported therethrough. The cover 72 is adhered to the skin 68 surrounding the wound by the adhesive coating 74 to provide a substantially air-tight seal over the wound. For a wound 50 of the type shown in FIG. 3A, the wound 50 having a tunneling portion 52, a packing 80 is preferably used to fill the open cavity of the wound 50 before applying the cover 72 by adhering the adhesive layer 74 to the skin 58 surrounding the wound 50.

When suction is applied by the negative pressure wound therapy system 70 to a wound 62 having the tunnel dressing 10 inserted thereinto, the suction is transmitted through the permeable material of the layer 14 and the sheath 12 to the wound tissue along the sides 66 and end 64 of the wound 62. The wound tissue is drawn against the wound contact surface 20, causing compression force on the dressing 10. In absorbing the compression force, the cavity 18 collapses inwardly, allowing at least a portion of the interstitial spaces within the support layer 14 and sheath 12 to remain open so that the suction can draw wound exudates out of the wound 62 through the wound cover 72 and into the conduit 76. Once the cavity 18 has collapsed, the support layer 14 can still be subjected to compressive forces due to the applied suction. The support layer is capable of resisting compression to maintain its fluid transport properties.

Preferably, the support layer 14 retains at least 10% of its original uncompressed volume when subjected to a suction of 75 mm Hg. In an embodiment, prior to the application of suction, the support layer 14 comprises about 5% polyester fibers and about 95% void space. In an embodiment, after application of a suction of 75 mm Hg, the support layer 14 retains about 75% of its original volume (so that the compressed layer 14, by volume, is about 7% fibers and 93% void space). To maintain adequate ability to transport wound exudates and provide suction to the wound tissue, the support layer preferably maintains at least about an equal amount of void space to the amount of fiber space, or about 10% of its original uncompressed volume (so that the compressed layer 14, by volume, is about 50% fibers and 50% void space).

Depending on the negative pressure wound therapy regimen, suction can be applied continuously or intermittently for periods ranging from a few hours to several days. When the time comes to remove or change the tunnel dressing 10, the clinician first removes the wound cover 72 and any packing 80 that may have been used. Then, grasping the portion of the dressing 10 protruding from the wound 62, the clinician gently pulls the dressing 10 to extract it from the tunnel wound 62. The structure of the dressing 10 is sufficiently strong that it retains its tensile strength even after being subjected to wound exudates and suction, such that the dressing does not tear or come apart as it is being removed. As discussed above with regard to FIG. 10 and a method of making the dressing 400, a weld 480 is formed extending along the inside of the dressing 400 from the distal end 446 to the proximal end 448. Similarly, in the tunnel dressing 10 as shown in FIGS. 1, 2, 4, 7A, and 7B, a weld (not shown) extends along the inside of the dressing 10 from the distal end 46 to the proximal end 48, the weld providing additional tensile strength to the dressing 10 to prevent tearing or breaking apart of the dressing 10 upon removal from the wound 62.

The tunnel dressing 10 can further be provided with regularly spaced markings 42 along the length of the sides 47 (i.e., from near the closed distal end 46 to near the open proximal end 48), as shown in FIG. 1. The markings 42 provide a visual indication of how deep the wound is, and can be used to determine the progress of a wound as it heals. The markings 42 also provide a measure to indicate how far the dressing 10 is partially withdrawn after it has been fully inserted, to leave sufficient space 90 for tissue growth in the wound end 64. The markings 42 can be made using a biocompatible ink, a series of slight depressions or protrusions from the surface 20 of the dressing 10, or other similar regularly repeated visual indicator.

The tunnel dressing 10 can also be provided with a visual marking 44 at the tip of the closed end 46, to provide assurance that the entire dressing 10 has been withdrawn. If a clinician withdraws the dressing 10 and the visual marking 44 is not present, the clinician is alerted that a part of the dressing 10 may remain within the wound cavity. The marking 44 is preferably made using a biocompatible ink, an embossing, or other similar identifiable visual indicator.

The support layer 14 of the tunnel dressing 10 can include structural features to enable the dressing 10 to resist compression when subjected to vacuum. Resisting compression enables good transport of wound exudates away from the wound surface 66 and out of the tunnel wound 62. In an embodiment, the layer 14 comprises randomly disposed fibers. In another embodiment, as shown in cross-section in FIG. 5, a support layer 30 comprises multiple structured voids or cavities 32 opening onto the inner surface 24 and extending into the layer 30. The structured voids 32 provide structural support to enable the layer 30 to resist compression under vacuum to both maintain the surface 20 of the dressing 10 in contact with the wound surface 66 and to keep open at least a portion of the interstitial spaces within the fibrous material of the layer 30 to provide for good fluid transport.

Figure 5:
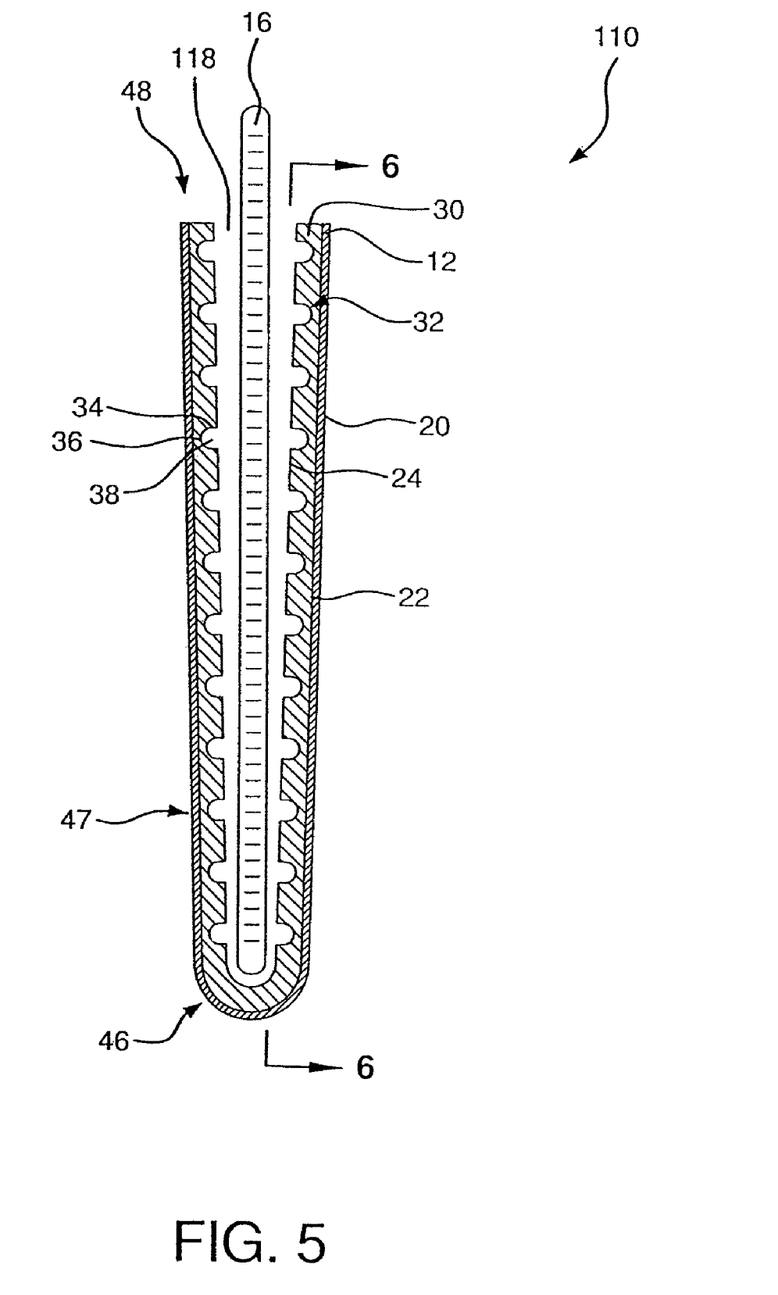
FIG. 5 is a cross-sectional view of an embodiment of the tunnel dressing of FIG. 1 taken through section 2-2.
Figure 6:
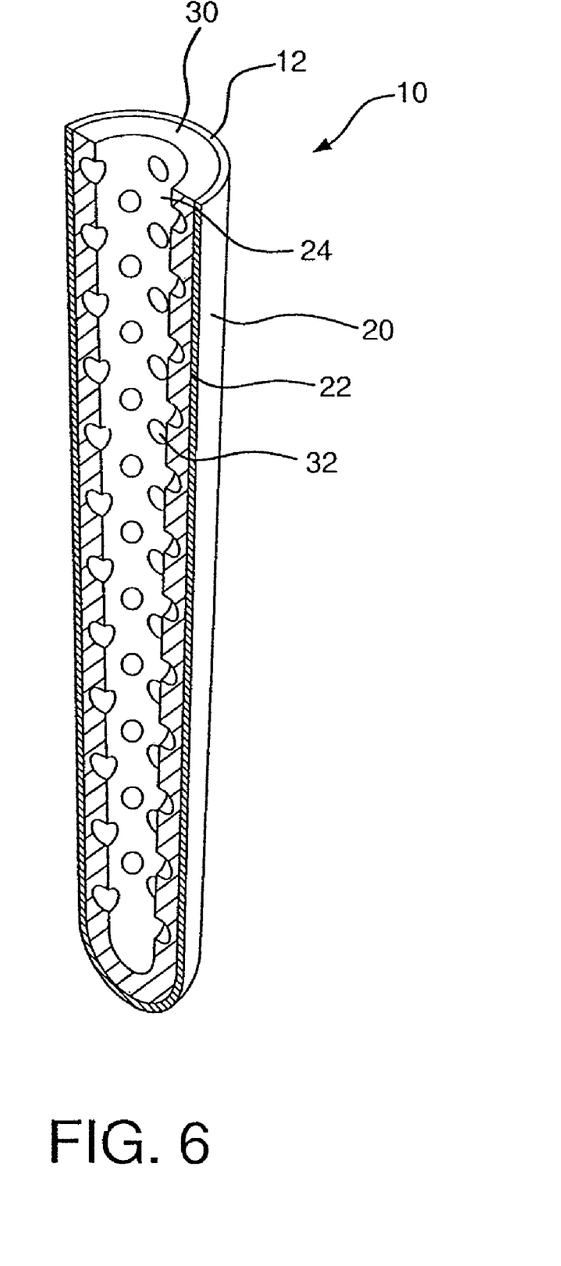
FIG. 6 is a partial perspective cross-sectional view of the tunnel dressing of FIG. 5.

Each void 32 comprises a cavity opening onto the inner surface 24 and extending a depth into the layer 30. The voids 32 may extend through the entire thickness of the layer 30, or may extending only to a depth that is less than the thickness of the layer 30. Each void 32 comprises sidewalls 34 extending generally perpendicularly to the surface 24, a cap 36 bridging the sidewalls to form a cavity within the void 32, and an opening 38 on the surface 24. The voids 32 are spaced apart in the material so that the openings 38 are correspondingly spaced apart on the surface 24. The width of the openings 38 in the surface 24 is preferably greater than about 0.1 mm and less than about 10 mm, more preferably between about 0.5 mm and about 5 mm, and most preferably about 2 mm. The depth of the voids 32, measured from the opening 38 in the surface 24 to the cap 36, is preferably greater than about 0.1 mm when suction is applied, more preferably between about 0.2 mm and 5 mm, and most preferably about 1.5 mm. The voids 32, are preferably dimple voids 32 that are generally circular in shape, as shown in FIG. 6, but can also be oblong, oval, square, triangular, channels, or other geometric shape capable of providing structural rigidity. The voids 32 can be formed into the layer 30 by several methods, including by heat stamping or vacuum forming, by applying molten material directly to a mold as in meltblowing, or by mixing fibers with an adhesive and spraying the mix onto a textured surface.

Figure 8:
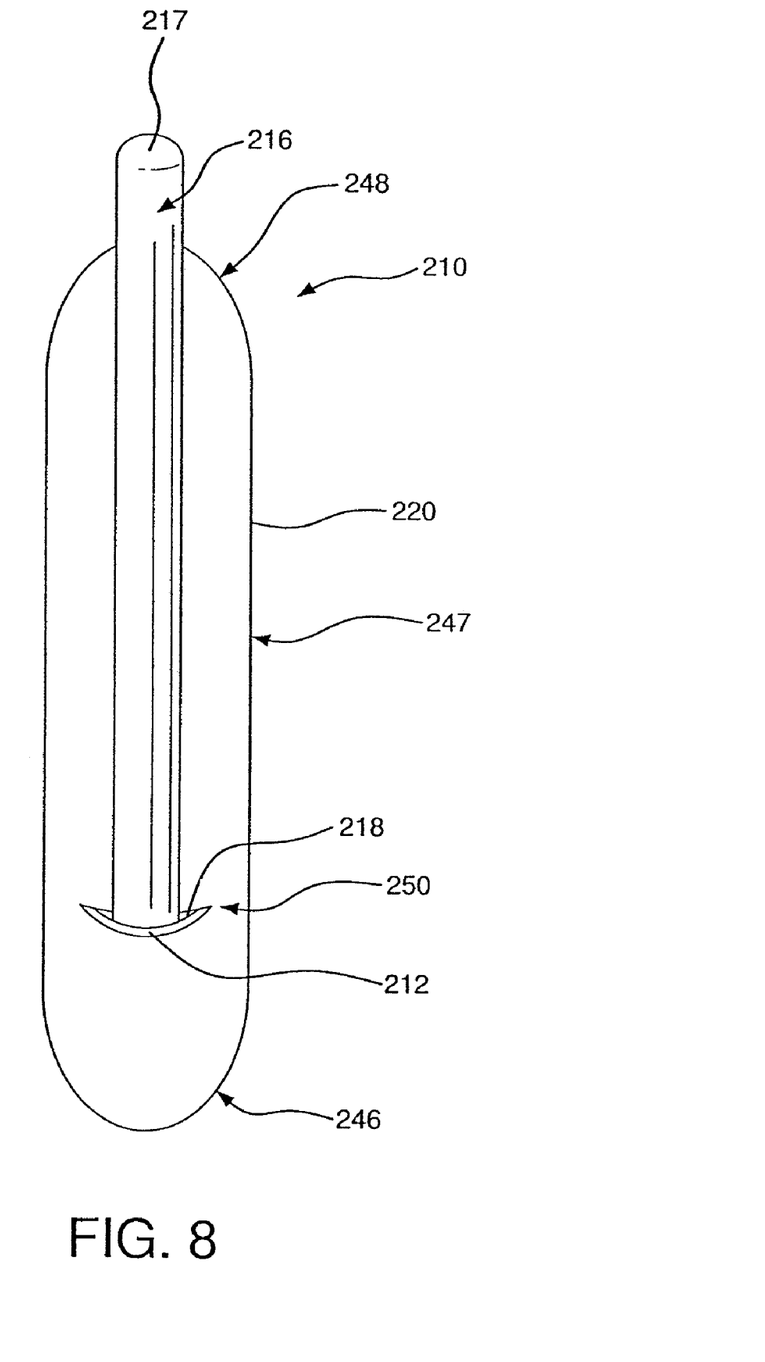
FIG. 8 is a perspective view of a tunnel dressing.

FIG. 8 shows another embodiment of a tunnel dressing 210 for treating a wound with suction. The tunnel dressing 210 is made from a permeable material 212 preferably having a fibrous structure similar to the support layer 14 in the tunnel dressing 10 of FIG. 1. The tunnel dressing 210 has a closed proximal end 248 and a closed distal end 246 spanned by at least a sidewall 247. The distal end 246 is adapted to enter a wound, so that when the dressing 210 is inserted into a tunneling wound, the distal end 246 is inserted first and leads the way into the depths of the wound. The tunnel dressing 210 further has an internal cavity 218 and a wound contact surface 220. The internal cavity 218 opens onto the wound contact surface 220 at an opening 250 disposed in the sidewall 247 between the proximal end 248 and the distal end 246. The cavity 218 extends at least from the opening 250 to near the distal end 246. The internal cavity 218 may also extend from the opening 250 toward the proximal end 248. An applicator rod 216 having a proximal portion 217 and a distal portion (not shown) can be used to guide the dressing 210 into a wound, the distal portion being removably disposed within the cavity 218 and the proximal portion 217 extending out from the tunnel dressing 210. After the dressing 210 is inserted into the wound, the rod 216 can be removed without disturbing the dressing 210 in the wound.

When the dressing 210 is formed from a fibrous material 212 such as polyester felt, the material 212 can be thermally seared along the outer wound contact surface 220 to minimize fiber shedding. Alternatively, the dressing 210 can be formed from a fibrous material 212 comprising a combination of polyester fibers and biocomponent fibers. Bicomponent fibers are fibers that have a core of one material and a sheath of a slightly different material. The material of the sheath preferably has a lower melting temperature than the material of the core so that products made from such fibers can be heated to a temperature that melts the sheath but not the core. The molten sheath material then locks or fuses the fibers together when cooled so that there is less shedding of fibers. In an embodiment, the dressing 210 could be formed from 85% standard polyester fiber and 15% bicomponent fibers having a polyester core with a 250° C. melting temperature and a copolyester sheath with a melting point ranging between about 110° C. and about 220° C. After it is formed into the desired shape, the material 212 of the dressing 210 could then be heated so that the sheath material melts to create a contact surface 220 less likely to shed fibers into the wound.

Figure 9:
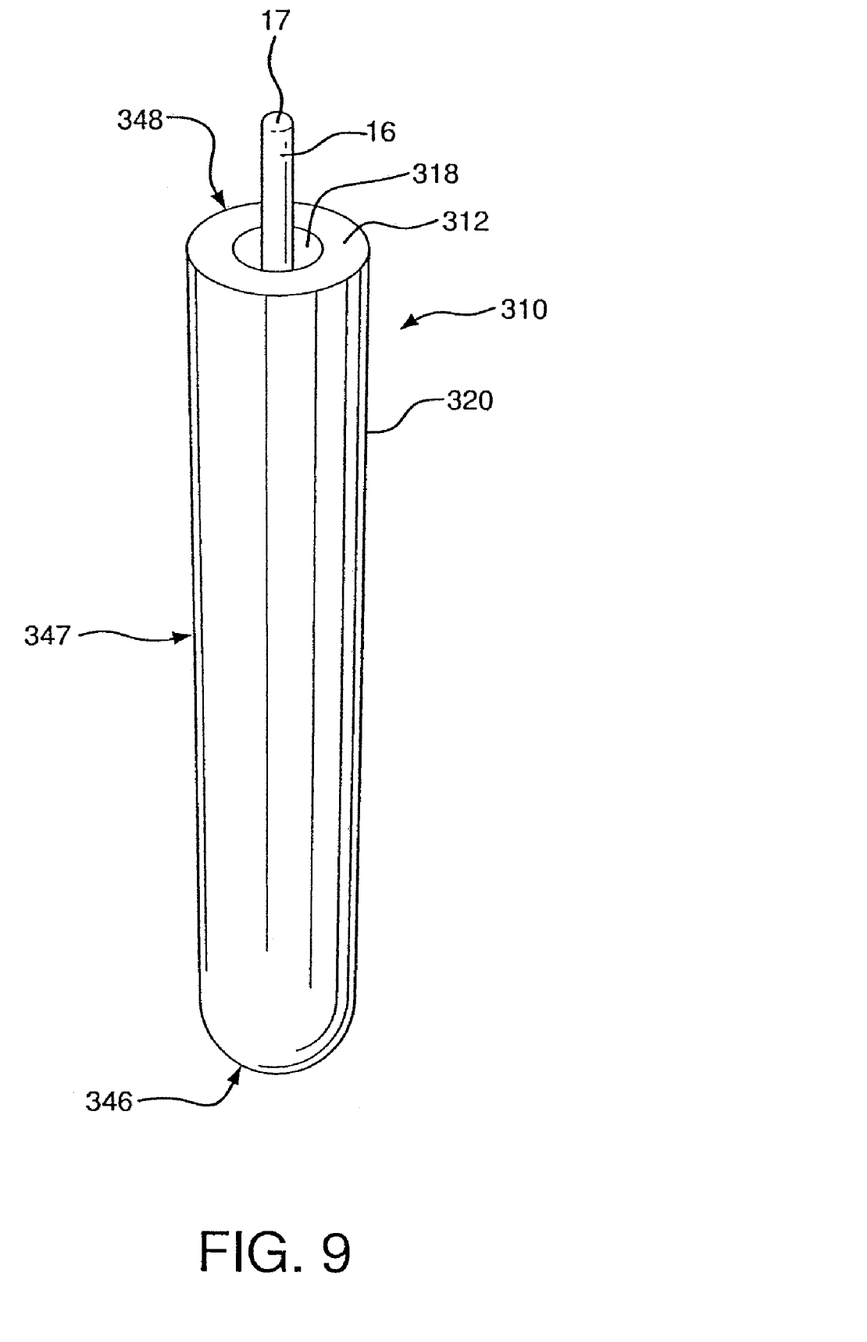
FIG. 9 is a perspective view of a tunnel dressing.

FIG. 9 shows another embodiment of a tunnel dressing 310 for treating a wound with suction. The tunnel dressing 310 is made from a permeable material 312 preferably having a fibrous structure similar to the support layer 14 in the tunnel dressing 10 of FIG. 1. The tunnel dressing 310 has an open proximal end 348 and a closed distal end 346 adapted to enter a wound, so that the when the dressing 310 is inserted into a tunneling wound, the distal end 346 is inserted first and leads the way into the depths of the wound. The tunnel dressing 310 further includes an internal cavity 318 and a wound contact surface 320. The internal cavity 318 opens onto the proximal end 348 of the dressing 310 and extends within the dressing 310 to near the distal end 346. An applicator rod 16 having a proximal portion 17 and a distal portion (not shown) can be used to guide the dressing 310 into a wound, the distal portion being removably disposed within the cavity 318 and the proximal portion 17 extending out from the tunnel dressing 310. After the dressing 310 is inserted into the wound, the rod 16 can be removed without disturbing the dressing 310 in the wound. The wound contact surface 320 of the dressing 310 can be prepared in any of the manners previously discussed with regard to the wound contact surface 220 of the dressing 210 shown in FIG. 8.

While the invention has been disclosed with reference to certain preferred embodiments, numerous modifications, alterations, and changes to the described embodiments are possible without departing from the sphere and scope of the invention, as defined in the appended claims and equivalents thereof. Accordingly, it is intended that the invention not be limited to the described embodiments, but that it have the full scope defined by the language of the following claims.

We claim:

1. A method of making a tunnel dressing for use in treating a tunneling wound with suction comprising:
   forming a stack comprising at least two layers;
   welding the at least two layers together to form a unitary piece;
   trimming excess material away from the unitary piece between the weld and the edges of the sheets to form the tunnel dressing having at least three sealed edges and an opening;
   inverting the article to form the tunnel dressing having an internal weld; and
   wherein the article has four sealed edges and wherein the opening is formed by cutting through one of the layers of the two layers.

2. A method of making a tunnel dressing for use in treating a tunneling wound with suction comprising:
   forming a stack comprising at least two layers;
   welding the at least two layers together to form a unitary piece;

trimming excess material away from the unitary piece between the weld and the edges of the sheets to form the tunnel dressing having at least three sealed edges and an opening;

inverting the article to form the tunnel dressing having an internal weld; and wherein the ultrasonic welding forms a U-shaped weld to create the three sealed edges.

3. A method of making a tunnel dressing for use in treating a tunneling wound with suction comprising:

forming a stack comprising at least two layers;

welding the at least two layers together to form a unitary piece;

trimming excess material away from the unitary piece between the weld and the edges of the sheets to form the tunnel dressing having at least three sealed edges and an opening;

inverting the article to form the tunnel dressing having an internal weld; and wherein the ultrasonic welding forms an L-shaped weld to create two of the three sealed edges, the third sealed edge being created by the folded over first and second sheets.

4. A method of making a tunnel dressing for use in treating a tunneling wound with suction comprising:

forming a stack comprising at least two layers;

welding the at least two layers together to form a unitary piece;

trimming excess material away from the unitary piece between the weld and the edges of the sheets to form the tunnel dressing having at least three sealed edges and an opening;

inverting the article to form the tunnel dressing having an internal weld; and wherein the ultrasonic welding forms a generally rectangular weld, the method further comprising the step of cutting off a portion of the weld to create the un-sealed edge prior to the trimming step.

* * * * *